United States Patent [19]
Muscan

[11] 3,940,973
[45] Mar. 2, 1976

[54] METHOD FOR THE DETERMINATION OF SHRINKAGE EFFECT

[75] Inventor: Alexandru Ioan Muscan, Bucharest, Romania

[73] Assignee: Institutul de Cercetari si Proiectari Pentru Utilaj Chimic si Rafinarii, Bucharest, Romania

[22] Filed: Mar. 11, 1974

[21] Appl. No.: 449,838

[52] U.S. Cl. ............................................... 73/88 R
[51] Int. Cl.² ............................................ G01N 3/12
[58] Field of Search ........................... 73/102, 88 R

[56] References Cited
UNITED STATES PATENTS

| | | | |
|---|---|---|---|
| 3,755,658 | 8/1973 | Walters | 73/89 X |
| 3,826,902 | 7/1974 | Claxton et al. | 73/89 X |

*Primary Examiner*—Jerry W. Myracle
*Attorney, Agent, or Firm*—Karl F. Ross; Herbert Dubno

[57] ABSTRACT

A method of determining the shrinkage effect to be intentionally produced by the manufacturing process in the fabrication of high-pressure cylindrical vessels wherein test samples are cut from the cylindrical body and transducers are mounted upon the inner face thereof. The body is subjected to fluid pressure and a strain ($\epsilon_p$) is determined on two test samples cut from the body while the strain intensity ($\epsilon_{pa}$) at the apparent proportionality limit is determined via the transducers, by detecting the hoop strain ($\epsilon_{ipa}$) at the apparent proportionality limit ($\epsilon_{pa} = \alpha \epsilon_{ipa}$ where $\alpha$ is a proportionality factor depending upon the vessel shape). The shrinkage effect is related to the difference of $\epsilon_p$ and $\epsilon_{pa}$.

1 Claim, 4 Drawing Figures

METHOD FOR THE DETERMINATION OF SHRINKAGE EFFECT

FIELD OF THE INVENTION

The present invention relates to a method for the quantitative determination of the shrinkage effect produced by manufacturing in high-pressure cylindrical vessels.

BACKGROUND OF THE INVENTION

In the fabrication of high-pressure cylindrical vessels for use as storage tanks, reactors and the like, care is taken to provide shrinkage designed to produce an internal strain or pressure adapted to take up at least some of the pressure developed by a fluid within the vessel. The thickness of the vessel is dimensioned to bring about the desired strain or internal prestress so that, when the vessel is loaded, the outward forces are balanced by the prestress.

In determining the thickness of the vessel, the degree of prestress brought about by the manufacturing process must be established for various thicknesses and it has been the practice heretofore to evaluate the shrinkage effect by forming test samples and applying destructive or distortive testing techniques to determine the yielding and rupture characteristics of the samples. Models of the vessel may also be required for these conventional processes.

The prior-art techniques thus have the disadvantage that considerable time may be required for fabricating the test samples and providing the knowledge gained by testing them in the fabrication of full-scale vessels to be subjected to high pressures.

OBJECT OF THE INVENTION

It is the principal object of the present invention to provide a method of determining the shrinkage effect in highpressure cylindrical vessels whereby the aforementioned disadvantages are obviated and a highly accurate measure of the shrinkage effect can be obtained with minimum time and material loss.

SUMMARY OF THE INVENTION

This object and others which will become apparent hereinafter is attained, in accordance with the present invention, by my discovery that there is a relationship between parameters which may be measured directly upon the vessel by nondestructive techniques and parameters which may be obtained by measurements carried out on samples cut from the actual vessel itself which can yield a quantitative value representing the shrinkage effect.

The method according to the invention thus avoids the disadvantages discussed previously by enabling the correct dimensions of a vessel which has been manufactured with shrinkage to be established by determining the hoop or circumferential strain resulting from the shrinkage effect as the difference between the intensity of the strain at the apparent proportionality limit ($pa$) and established by transducers on the inner face of the vessel which is filled with a pressurizing fluid, e.g. oil, and the strain $\epsilon_p$ at the proportionality limit and determined separately by measuring transducers. The intensity of the strain at the apparent proportionality limit is determined from the hoop strain at the apparent proportionality limit corrected by an $\alpha$ coefficient which is a function of the vessel shape.

According to a feature of the invention, strain-measuring transducers, e.g. conventional strain gauges, are mounted on the inner face of the vessel and the pressure therewithin is raised by applying a pressure $p$ to liquid in the vessel and filling the latter until the strain $\epsilon_{ipa}$ at the apparent proportionality limit is met.

The critical relationship is:

$$\frac{p}{\epsilon_{ipa}} = C \begin{array}{l} +0\% \\ -5\% \end{array} \quad (1)$$

The strain $\epsilon_p$ at the proportionality limit of the material is determined separately on at least two test samples severed from the cylindrical body of the vessel and hence subjected to the same heat treatment and mechanical working characteristics of the vessel. These samples are tested on a machine capable of determining tensile strength and using conventional processes.

The strain-measuring transducers for the tensile-strength test are placed on each of the standard test samples at diametrical opposite location, i.e., are angularly offset by 180° and tensile stress $f$ is applied until the relationship:

$$\frac{f}{\epsilon_p} = C \begin{array}{l} +0\% \\ -5\% \end{array} \quad (2)$$

is met.

Since, during the hydraulic test, the vessel is subjected to three-dimensional stress while the strain measurement only provides the hoop strain $\epsilon_{ipa}$ at the apparent proportionality limit, it is necessary to provide a correction amounting for the strain intensity under three-dimensional stress. The equation for such correction is:

$$\epsilon_{pa} = \alpha \epsilon_{ipa} \quad (3)$$

In this relationship, $\epsilon_{pa}$ represents the three-dimensional strain intensity while $\alpha$ is a shape coefficient determined by the relationship:

$$\alpha = \frac{C}{\sqrt{3}} \cdot \frac{(1+\mu)\frac{\gamma_n^2}{\gamma_o^2}}{(1+\mu)\frac{\gamma_n^2}{\gamma_o^2}+(1+2\mu)} \quad (4)$$

where $C$ is a constant characteristic of the material, $\mu$ is POISSON'S ratio, $\nu_n$ is the outer radius of the cylindrical body and $\gamma_o$ is the internal radius thereof.

The hoop strain $\epsilon_{if}$ resulting from the shrinkage effect is the difference between the strain intensity $\epsilon_{pa}$ at the apparent proportionality limit, determined as above, and the strain $\epsilon_p$ of the material as determined on the test samples.

Thus:

$$\alpha_{if} = \epsilon_{pa} - \epsilon_p \quad (5)$$

$$\alpha_{if} = \alpha \epsilon_{ipa} - \epsilon_p \quad (6)$$

BRIEF DESCRIPTION OF THE DRAWING

The above and other objects, features and advantages of the present invention will become more readily apparent from the following description, reference being made to the accompanying drawing in which.

SPECIFIC DESCRIPTION AND EXAMPLE

Figure 3:
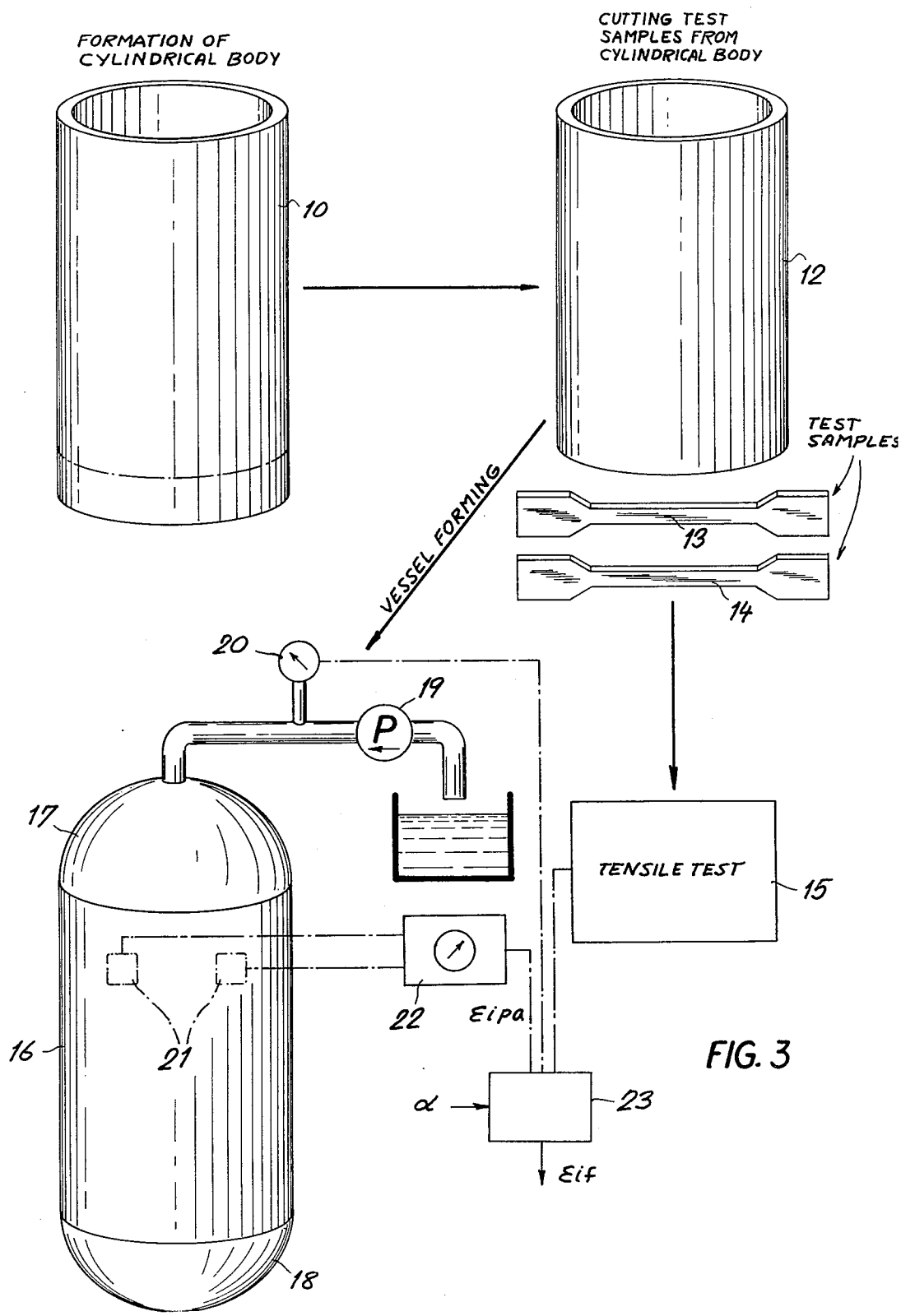
FIG. 3 is a diagram illustrating the principles of the present invention.

From FIG. 3 it will be apparent that a cylindrical vessel 10 is formed by any conventional technique (multilayer, multiwall, coil layer, wicked tape, etc.) wherein a shrinkage of the body gives rise to a circumferential internal stress or shrinkage effect for the cylindrical structure 12 from which at least two standard test samples 13 and 14 are severed. The test samples are subjected to tensile testing at 15 to establish the value of the strain $\epsilon_p$ at the proportionality limit.

Figure 2A:
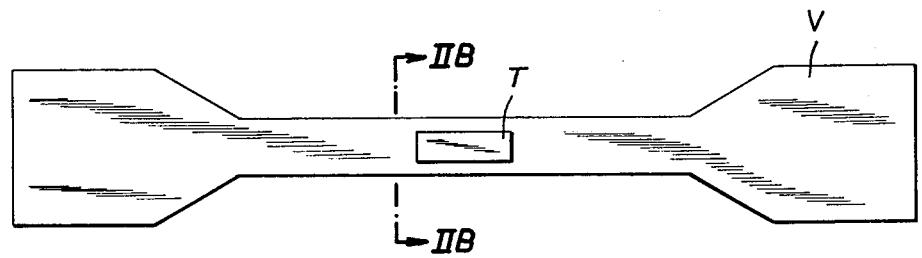
FIG. 2A is an elevational view of a test sample.
Figure 2B:
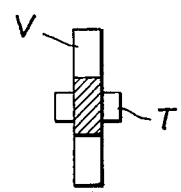
FIG. 2B is a section through a test sample provided with strain gauges for tensile stressing along line IIB — IIB of FIG. 2A.

As shown in FIGS. 2A and 2B, this is accomplished by applying a pair of strain gauges T to the sample V at diametrically opposite locations and generating the tensile force $f$ until the ratio of the strain gauge output and the force reaches a constant as noted in relationship (2).

The body 12 is formed into a vessel 16 by applying the domes 17 and 18 and is pressurized with oil by a hydraulic pump 19, the pressure $p$ within the vessel being read upon a gauge 20. Strain gauges 21 are connected to the usual output circuitry 22 so that the hoop strain $\epsilon_{ipa}$ at the apparent proportionality limit is determined using relationship (1), $C$ being a constant.

Figure 1:
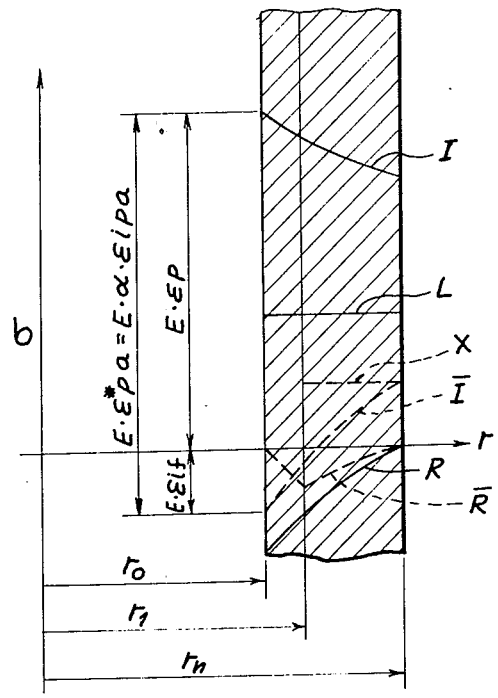
FIG. 1 is a cross-section through the material of the vessel showing the various strain relationships.

From FIG. 1 it may now be noted that I represents the hoop stress caused by the liquid head, R the radial stress produced by the liquid head and L the axial stress produced by the liquid head. $X$ is the shrinkage stress while $\bar{I}$ is the hoop stress resulting from shrinkage and $\bar{R}$ is the radial stress resulting from shrinkage. Since the shrinkage effect in the circumferential direction can be represented by the relationship (referring to FIG. 1):

$$I_o = X \cdot I_n \frac{\gamma_n^2 - \gamma_o^2}{\gamma_1^2 - \gamma_o^2} \tag{7}$$

it is possible to write:

$$E \cdot \epsilon_{if} I_o = X \cdot I_n \frac{\gamma_n^2 - \gamma_o^2}{\gamma_1^2 - \gamma_o^2} \tag{8}$$

and the average tensil stress of shrinkage is:

$$X = \frac{E \cdot (\alpha \cdot \epsilon_{ipa} - \epsilon_p)}{I_n \left( \frac{\gamma_n^2 - \gamma_o^2}{\gamma_1^2 - \gamma_o^2} \right)} \tag{9}$$

In the foregoing $E$ is the modulus of elasticity and $I_o$ is the hoop stress under shrinkage.

Since all of the values on the right-hand side of the last relationship are known or have been determined as described above, it is possible to establish the thickness of the vessel for a given shrinkage stress for a given vessel and thereby establish its pressurizing capacity or to determine the shrinkage stress for a given thickness of the vessel wall.

In FIG. 3, block 23 functions as a calculator automatically producing the value $\epsilon_{if}$ from the difference between $\epsilon_{pa}$ and $\epsilon_p$ in accordance with the algorithm represented by relationships (8) and (9).

I claim:

1. A method of determining the shrinkage effect for a high-pressure cylindrical vessel in the body of which a shrinkage effect $\epsilon_{if}$ is induced, comprising subjecting a plurality of standard test samples from said body to tensile stress to determine the strain $\epsilon_p$ at the proportionality limit; applying strain gauges to said body and pressurizing the same with a fluid to determine the hoop strain $\epsilon_{ipa}$ at the apparent proportionality limit; deriving the strain intensity $\epsilon_{pa}$ at the apparent proportionality from the hoop strain $\epsilon_{ipa}$ corrected by a coefficient determined by the vessel shape, and determining the hoop strain $\epsilon_{if}$ as the difference between $\epsilon_{pa}$ and $\epsilon_p$.

* * * * *